United States Patent

Kondo et al.

Patent Number: 5,098,907
Date of Patent: * Mar. 24, 1992

[54] POWDERY PHARMACEUTICAL COMPOSITION CONTAINING BENZOYL UREA, A DISPERSANT AND SILICIC ACID

[75] Inventors: Nobuo Kondo; Masahiro Kikuchi; Tsunetaka Nakajima; Masahiro Watanabe; Kouichi Yamauchi, all of Hirakata; Takahiro Haga, Kusatsu; Nobutoshi Yamada, Kusatsu; Hideo Sugi, Kusatsu; Toru Koyanagi, Kusatsu, all of Japan

[73] Assignees: Ishihara Sangyo Kaisha Ltd.; The Green Cross Corporation, both of Osaka, Japan

[*] Notice: The portion of the term of this patent subsequent to Jul. 18, 2006 has been disclaimed.

[21] Appl. No.: 469,054

[22] Filed: Jan. 23, 1990

[30] Foreign Application Priority Data

Jan. 24, 1989 [JP] Japan .................. 1-15626

[51] Int. Cl.$^5$ ............. A61K 31/505; A61K 31/44; A61K 33/00
[52] U.S. Cl. ..................... 514/274; 514/351; 514/975; 424/600; 424/724
[58] Field of Search ............ 514/274, 349, 351, 975; 424/600, 724

[56] References Cited

U.S. PATENT DOCUMENTS

| | | | |
|---|---|---|---|
| 4,173,638 | 11/1979 | Nishiyama et al. | 514/351 |
| 4,677,111 | 6/1987 | Haga et al. | 514/274 |
| 4,727,077 | 2/1988 | Haga et al. | 514/274 |
| 4,798,839 | 1/1989 | Ayad | 514/351 |
| 4,849,425 | 7/1989 | Kondo et al. | 514/274 |
| 4,863,924 | 9/1989 | Haga et al. | 514/247 |
| 4,904,668 | 2/1990 | Kondo et al. | 514/274 |

FOREIGN PATENT DOCUMENTS

| | | |
|---|---|---|
| 0264904 | 4/1988 | European Pat. Off. |
| 60-104067 | 6/1985 | Japan .................. 514/349 |
| 61-191623 | 8/1986 | Japan . |
| 61-205257 | 9/1986 | Japan . |

Primary Examiner—Richard L. Raymond
Assistant Examiner—Gary E. Hollinden
Attorney, Agent, or Firm—Oblon, Spivak, McClelland, Maier & Neustadt

[57] ABSTRACT

A powdery pharmaceutical composition comprising a benzoyl urea compound of the formula:

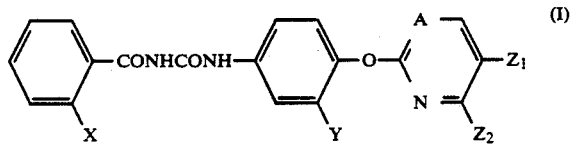

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is CH or a nitrogen atom, as an active ingredient, a nonionic surfactant as a dispersant, at least one member selected from the group consisting of sugar, sugar-alcohol and a nonionic surfactant as a disintegrant, and anhydrous silicic acid as a fluidizer.

7 Claims, No Drawings

POWDERY PHARMACEUTICAL COMPOSITION CONTAINING BENZOYL UREA, A DISPERSANT AND SILICIC ACID

The present invention relates to a powdery pharmaceutical composition containing a benzoyl urea compound as the main component.

Heretofore, a benzoyl urea compound represented by the following formula I is per se known:

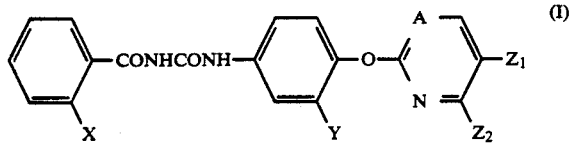

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is =CH— or a nitrogen atom.

Further, it is known that such a benzoyl urea compound shows an excellent antitumorous action (e.g. Japanese Unexamined Patent Publications No. 109721/1982, No. 1670/1986, No. 93163/1986 and No. 205257/1986). This compound is hardly soluble in water and thus poor in the absorbability e.g. from the gut. Accordingly, in order to obtain an adequate antitumorous action, it is necessary to increase the dose, and there is a possibility of adverse effects by such a large dose.

Under the circumstances, some pharmaceutical compositions have been proposed which are capable of providing excellent absorbability from the gut for the benzoyl urea compound of the formula I (Japanese Unexamined Patent Publication No. 185013/1987 and European Unexamined Patent Publication No. 264904).

From the viewpoint of drug formulation engineering, in the case of such pharmaceutical compositions excellent in the absorbability, they are preferably in a powder form so long as they have such characteristics as being free from blocking and excellent in the flowability, since the compositions in a powder form are convenient for handling during formulation, packaging or subdividing, they can easily be administered to patients, and the absorbability of the benzoyl urea compound of the formula I e.g. from the gut will thereby be improved.

Accordingly, it is an object of the present invention to provide a pharmaceutical composition containing a benzoyl urea compound of the formula I, which has excellent flowability and little blocking tendency, when formed into a powdery drug formulation.

The present inventors have conducted various studies in view of the above problems and have found it possible to obtain a powdery pharmaceutical composition having improved flowability and little blocking tendency by incorporating a specific disintegrator, a specific dispersant and a specific fluidizer, preferably in a specific order, to the benzoyl urea compound of the formula I. The present invention has been accomplished on the basis of this discovery.

Namely, the present invention provides a powdery pharmaceutical composition comprising a benzoyl urea compound of the formula:

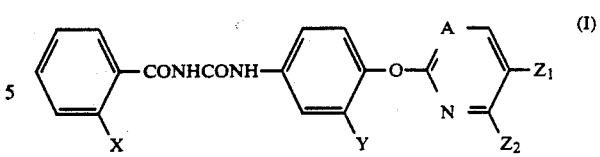

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is CH or a nitrogen atom, as an active ingredient, a nonionic surfactant as a dispersant, at least one member selected from the group consisting of sugar, sugar-alcohol and a nonionic surfactant as a disintegrant, and anhydrous silicic acid as a fluidizer.

Particularly, the present invention provides a powdery pharmaceutical composition in the form of freeze-dried formulation manufactured by a process which comprises pulverizing the benzoyl urea compound in an aqueous solution containing the dispersant, adding the disintegrant to the resulting liquid formulation, lyophilizing the mixture, and adding the fluidizer thereto.

Now, the present invention will be described in detail with reference to the preferred embodiment.

The benzoyl urea compound of the formula I as the present invention includes, for example, compounds of the following formulas:

(Compound No. 1)

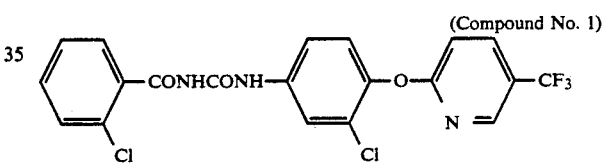

(Compound No. 2)

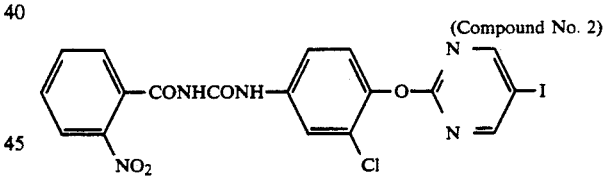

(Compound No. 3)

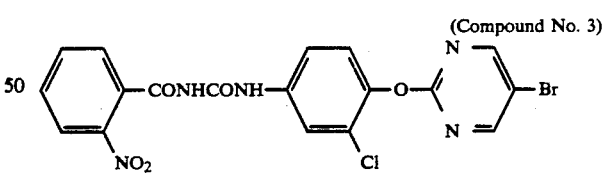

(Compound No. 4)

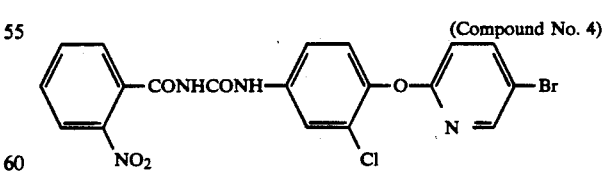

(Compound No. 5)

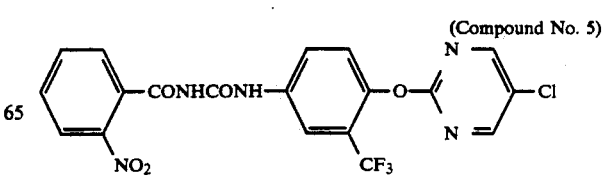

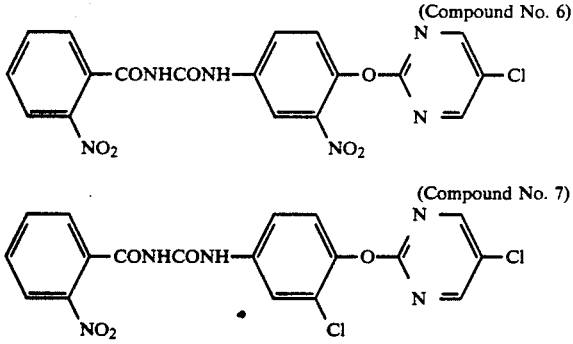

The benzoyl urea compound of the formula I is per se known and can be produced by the method described in Japanese Unexamined Patent Publication NO. 109721/1982 or by a method similar thereto.

For the preparation of the pharmaceutical composition of the present invention, the benzoyl urea compound of the formula I is preferably as fine as possible.

The dispersant used in the present invention serves as a dispersing agent when the benzoyl urea compound of the formula I is suspended and pulverized in water. A nonionic surfactant may be used as the dispersant in the present invention without any particular limitation so long as the object of the present invention can thereby be attained, and it can be used as a pharmaceutically acceptable additive. Particularly preferred is the one in which the hydrophile-lipophile balance is more than 3. Specific examples of such a dispersant include a polyoxyethylene hardened castor oil, a polyoxyethylene polyoxypropylene glycol, a sugar fatty acid ester, a glycerine fatty acid ester, a sorbitan fatty acid ester, a propylene glycol fatty acid ester, a polyglycerine fatty acid ester, a polyoxyethylene sorbitan fatty acid ester, a polyoxyethylene sorbit fatty acid ester, a polyoxyethylene glycerine fatty acid ester, a polyethylene glycol fatty acid ester and a polyoxyethylene castor oil. Among these nonionic surfactants, preferred are the polyoxyethylene hardened castor oil, the polyoxyethylene polyoxypropylene glycol and the polyglycerine fatty acid ester.

The disintegrant in the present invention is incorporated primarily to enhance the granularity and disintegratability at the time of lyophilizing the benzoyl urea compound of the formula I.

As such a disintegrant, there may be mentioned a sugar, a sugar alcohol and a nonionic surfactant.

As the sugar for the disintegrant, there may be mentioned a monosaccharide (such as glucose or fructose), a disaccharide (such as lactose or sucrose) and a polysaccharide (such as starch, dextrin or cellulose).

As the sugar alcohol for the disintegrant, there may be mentioned mannitol and sorbitol.

The nonionic surfactant useful as the disintegrant includes, for example, a polyoxyethylene hardened castor oil, a polyoxyethylene polyoxypropylene glycol, a sucrose fatty acid ester, a glycerine fatty acid ester, a sorbitan fatty acid ester, a propylene glycol fatty acid ester, a polyglycerine fatty acid ester, a polyoxyethylene sorbitan fatty acid ester, a polyoxyethylene sorbit fatty acid ester, a polyoxyethylene glycerine fatty acid ester, a polyethylene glycol fatty acid ester and a polyoxyethylene castor oil.

The nonionic surfactant is preferably used as the disintegrant. Particularly preferred is the sucrose fatty acid ester or polyoxyethylene polyoxypropylene glycol.

Although the same nonionic surfactant may be used both as the dispersant and as the disintegrant, different ones are preferably used. For example, when the polyglycerine fatty acid ester (e.g. decaglycerine monolaurate) or the polyoxyethylene hardened castor oil (e.g. polyoxyethylene hardened castor oil 60) is used as the dispersant, it is preferred to use the sucrose fatty acid ester as the disintegrant.

The fluidizer used in the present invention has functions to improve the flowability and to prevent the powder from blocking when the pharmaceutical composition is formulated in a powder form. As the fluidizer in the present invention, anhydrous silicic acid is employed. As the anhydrous silicic acid, light anhydrous silicic acid may be mentioned.

The pharmaceutical composition of the present invention, particularly the freeze-dried formulation, can be prepared by pulverizing the benzoyl urea compound of the formula I in an aqueous suspension containing the dispersant, then adding the disintegrant thereto, lyophilizing the mixture, and adding the fluidizer thereto.

The pulverization is carried out preferably in a wet system. The pulverization in a wet system is a method wherein the material to be pulverized is rotated or shaked together with beads (particularly glass beads) in the liquid containing a dispersant. A machine such as Dino-mill (KDL type, made by Willy A Bachofen Company) may be used for the method. At the time of the pulverization, the concentration of the benzoyl urea compound in the aqueous solution is from 1 to 70%, preferably form 20 to 50%, by weight/volume. The concentration in such a range is preferable particularly when Dino-mill is used for pulverization in a wet system. The concentration of a nonionic surfactant as the dispersant is from 1 to 30%, preferably from 2 to 20%, by weight/volume. The diameter of the glass beads to be used, is usually in a range of from 0.1 to 1.5 mm, preferably from 0.25 to 0.5 mm. The pulverization time is usually in a range of from 5 to 60 minutes.

The composition which has been pulverized in a wet system by using the above mentioned conditions, has a mean particle diameter of from 0.2 to 1.0 μm (as measured by a photo scattering method).

After the pulverization in a wet system, the glass beads are removed by a sieve. The disintegrant is then added to the liquid of the pulverized benzoyl urea compound of the formula I, followed by lyophilization. The concentration of the disintegrant is in a range of from 1 to 90%, preferably from 10 to 70%, by weight/volume.

After the lyophilization, the fluidizer is uniformly mixed to the freeze-dried powder to obtain a pharmaceutical composition of the present invention in a particularly preferred form of a freeze-dried formulation. The amount of the fluidizer t be incorporated here is usually from 1 to 20 parts by weight, preferably from 4 to 20 parts by weight, relative to 100 parts by weight of the dried powder.

The pharmaceutical composition, particularly the freeze-dried formulation, of the present invention, preferably has a composition by a weight ratio of e.g. benzoyl urea compound of the formula I:dispersant:disintegrant:fluidizer = 1 to 70:1 to 30:1 to 90:1 to 20, preferably 20 to 50:2 to 10:10 to 70:4 to 20.

The pharmaceutical composition, particularly the freeze-dried formulation, of the present invention can further be formed into various optional drug formulations by conventional methods. Such optional drug formulations include, for example, formulations for oral administration such as pulveres, microgranules, granules, capsules and tablets.

For the preparation of such formulations, starch, cellulose, lactose, sodium carboxymethyl starch, sodium carboxymethyl cellulose, etc. may be used as excipients.

The pharmaceutical composition, particularly the freeze-dried formulation, of the present invention is usually orally administered to mammals including human, cattle, horses, dogs, rats and mice. The dose may vary depending upon e.g. the diseased state, the sex, the body weight and the type of formulation. However, in the case of oral administration of the composition of the present invention against human malignant lymphoma or lung cancer, a daily dose of the benzoyl urea compound of the formula I for an adult is from 5 to 100 mg/kg body weight, and such a dose is administered from once to third times per week.

The powdery pharmaceutical composition, particularly the freeze-dried formulation, of the present invention has flowability and anti-blocking tendency and is excellent in the granularity, the disintegratability and the stability. Further, the absorbability of the benzoyl urea compound of the formula I from the gut is thereby remarkably improved.

Accordingly, by using the pharmaceutical composition, particularly the freeze-dried formulation, of the present invention, the handling for the preparation of drug formulations or for packaging or subdividing, will be easy, and the administration to a patient will be easy. Further, it is thereby possible to reduce the dose of the benzoyl urea compound of the formula I, whereby it is possible to reduce the pain to the patient during the administration or to reduce side effects.

Now, the present invention will be described in further detail with reference to Examples and Test Examples. However, it should be understood that the present invention is by no means restricted to such specific Examples.

EXAMPLE 1

Compound 3 (20 g) was suspended in 50 ml of a 5 w/v % polyoxyethylene hardened caster oil (HCO-60) aqueous solution and subjected to wet pulverization by Dino-mill (3,000 rpm for 45 minutes) using 50 g glass beads (diameter: 0.25–0.5 mm). After completion of the pulverization, glass beads were removed by a sieve to obtain a wet-pulverized formulation of Compound 3. To 50 ml of this liquid formulation, 20 g of sucrose monopalmitic acid ester (P1670, manufactured by Mitsubishi Kasei Corporation) was added, and the mixture was freezed by dry ice-methanol and subjected to vacuum drying for 24 hours to remove water. Further, 4 g of light silicic acid anhydride was added and mixed thereto to obtain a pulvis.

EXAMPLE 2

Compound 3 (15 g) was suspended in 50 ml of a 5 w/v % polyoxyethylene polyoxypropylene glycol (Pluronic F68) aqueous solution and subjected to wet pulverization by Dino-mill (3,000 rpm for 45 minutes) using 50 g of glass beads (diameter: 0.25–0.5 mm). After completion of the pulverization, the glass beads were removed by a sieve to obtain a wet pulverized formulation of Compound 3.

To 50 ml of this liquid formulation, 30 g of sucrose monopalmitic acid ester (P1670, manufactured by Mitsubishi Kasei Corporation) was added, and the mixture was freezed by dry ice-methanol and then subjected to vacuum drying for 24 hours to remove water. Further, 4 g of light silicic acid anhydride was added and mixed thereto to obtain a pulvis.

EXAMPLE 3

A pulvis was prepared in the same manner as in Example 2 except that instead of the polyoxyethylene polyoxypropylene glycol, decaglycerin monolaurate (Decaglin 1 L, manufactured by Nikko Chemical Company) was used.

EXAMPLE 4

In the same manner as in Example 3, a pulvis having the following composition was prepared.

| | |
|---|---|
| Compound 3 (main ingredient) | 316 mg |
| Decaglycerin monolaurate (decaglycerin 1 L, dispersant) | 53 mg |
| Sucrose monopalmitic acid ester (P-1670, disintegrater) | 631 mg |
| Total | 1000 mg |

To 100 mg of the above pulvis, 8 mg of light silicic acid anhydride and 100 mg of corn starch were added, and after an addition of isopropyl alcohol, the mixture was kneaded, then dried and sieved through a screen of 30 mesh to obtain granules (wet system granulation).

Further, using crystalline cellulose or lactose instead of the corn starch, granules were prepared in the same manner.

EXAMPLE 5

To 100 mg of the pulvis in Example 4, 10 mg of sodium carboxymethylcellulose, 4 mg of light silicic acid anhydride and 2 mg of magnesium stearate were added. The mixture was mixed and tabletted. The tablets were pulverized in a mortar and then sieved through a screen to obtain granules of from 12 to 50 mesh (dry system granulation).

Further, using 50 mg of corn starch or 30 mg of sodium carboxymethylstarch, instead of 10 mg of sodium carboxymethylcellulose, granules were prepared in the same manner.

TEST EXAMPLE 1

| Known composition: | |
|---|---|
| Compound 3 (main ingredient) | 316 mg |
| Decaglyne 1-L (dispersant) | 53 mg |
| Sucrose fatty acid ester P-1670 (disintegrater) | 631 mg |
| Total | 1000 mg |

On the basis of the above known composition, improvement of the flowabiliaty of the powdery composition and prevention of blocking were studied to improve the easiness for administration or the efficiency for the production, particularly for subdivided packaging.

After adding and mixing magnesium stearate, light silicic acid anhydride or a mixture thereof, as the fluidizer, to the above known composition, at a concentration as shown bellow, the flowability and blocking tendency were visually observed.

Amount of magnesium stearate: 1, 2, 4, 6 or 8%
Amount of light silicic acid anhydride: 1, 2, 4 or 8%
Amount of 4% magnesium stearate +2% light silicic anhydride: 6%

After adding and mixing magnesium stearate, light silicic acid anhydride or a mixture thereof, as the fluidizer, to the above known composition, the flowability and blocking tendency of the composition, were as follows.

Namely, by an addition of magnesium stearate in an amount of at least 4%, an improvement in the flowability was observed, but even by an addition of 8%, the composition underwent coagulation simply by lightly pressing it with a finger and showed a blocking phenomenon. By an addition of light silicic anhydride in an amount of at least 2%, an improvement in the flowability was observed, and by the addition in an amount of 8%, adequate improvement in the anti-blocking tendency was observed. By an addition of 4% magnesium stearate +2% light silicic anhydride, a blocking phenomenon was observed.

TEST EXAMPLE 2

| Pulvis according to the present invention: | |
| --- | --- |
| Compound 3 | 292 mg |
| Decaglin 1-L | 49 mg |
| P-1670 | 585 mg |
| Light silicic acid anhydride | 74 mg |
| Total | 1000 mg |

The physical properties of the above dust of the present invention will be shown below. The physical properties were measured by a powder tester (manufactured by Hosokari Micron).

1. Flow Properties

Angle of repose: 40°
Spatula angle: 58°
Loose apparent specific gravity: 0.43 g/ml
Packed apparent specific gravity: 0.57 g/ml
Compressibility: 24.5%
Uniformity: 2.94
Degree of flowability: Fairly good 2. Jetting Properties Flow index: 72.5
Disintegration angle: 22°
Difference angle: 18°
Dispersibility: 7.2%
Degree of jetting: Fairly strong

TEST EXAMPLE 3

(Absorption by Rats)

With respect to the pulvis according to the composition of the present invention and the pulvis according to the known composition, the concentrations of Compound 3 in the plasma of the respective rats by oral administration and AUC were compared. The results are shown in Table 1.

The conditions were as follows:
Dose: 50 mg (as Compound 3)/5 ml of water/kg of the body weight, was orally administered.
Animals: SD type male rats (body weight: 180–200 g), five animals per group
Blood sampling: 1, 3, 6, 8, 10 and 24 hours later
Quantitative analysis:
HPLC method [Column: $C_{18}$ reversed phase system; Mobile phase: acetonitrile-water system; Detection: ultraviolet absorption (wavelength: 265 nm)]

TABLE 1

| | | Pulvis of the present invention | Known pulvis |
| --- | --- | --- | --- |
| Concentration in plasma ($\mu$g/ml) | Immediately after administration | 0 | 0 |
| | 1 hr | 0.28 ± 0.03 | 0.24 ± 0.03 |
| | 2 hrs | 0.46 ± 0.09 | 0.40 ± 0.07 |
| | 6 hrs | 0.52 ± 0.21 | 0.51 ± 0.09 |
| | 8 hrs | 0.51 ± 0.19 | 0.47 ± 0.10 |
| | 10 hrs | 0.46 ± 0.21 | 0.46 ± 0.13 |
| | 24 hrs | 0.35 ± 0.05 | 0.26 ± 0.09 |
| AUC (0–24 hrs) ($\mu$g · hr/ml) | | 10.67 | 9.07 |

We claim:

1. A powdery pharmaceutical composition comprising a benzoyl urea compound of the formula:

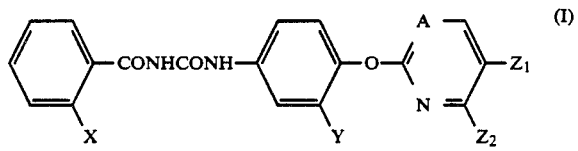

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom, and A is CH or a nitrogen atom, as an active ingredient, a nonionic surfactant as a dispersant, at least one member selected from the group consisting of sugar, sugar-alcohol and a nonionic surfactant as a disintegrant, and anhydrous silicic acid as a fluidizer.

2. The composition according to claim 1, wherein the benzoyl urea compound is selected from the group consisting of N-(2-chlorobenzoyl)-N'-[3-chloro-4-(5-trifluoromethyl-2-pyridinyloxy)phenyl]urea, N-(2-nitrobenzoyl)-N'-[3-chloro-4-(5-iodo-2-pyrimidinyloxy)phenyl]urea, N-(2-nitrobenzoyl)-N'-[3-chloro-4-(5-bromo-2-pyrimidinyloxy)phenyl]urea, N-(2-nitrobenzoyl)-N'-[3-chloro-4-(5-chloro-2-pyrimidinyloxy)phenyl]urea, N-(2-nitrobenzoyl-N'-[3-trifluoromethyl-4-(5-chloro-2-pyrimidinyloxy)phenyl]urea and N-(2-nitrobenzoyl)-N'-[3-nitro-4-(5-chloro-2-pyrimidinyloxy)phenyl]urea.

3. The composition according to claim 1, wherein the benzoyl urea compound is selected from the group consisting of N-(2-nitrobenzoyl)-N'-[3-chloro-4-(5-iodo-2-pyrimidinyloxy)phenyl]urea, N-(2-nitrobenzoyl)-N'-[3-chloro-4-(5-bromo-2-pyrimidinyloxy)phenyl]urea and N-(2-nitrobenzoyl)-N'-[3-chloro-4-(5-chloro-2-pyrimidinyloxy)phenyl]urea.

4. The composition according to claim 1, wherein the benzoyl urea compound is N-(2-nitrobenzoyl)-N'-[3-chloro-4-(5-bromo-2-pyrimidinyloxy)phenyl]urea.

5. The composition according to claim 1, wherein the benzoyl urea compound is N-(2-nitrobenzoyl)-N'-[3-chloro-4-(5-chloro-2-pyrimidinyloxy)phenyl]urea.

6. The composition according to claim 1, which comprises from 1 to 70 by weight of the benzoyl urea compound, from 1 to 30 by weight of the dispersant, from 1 to 90 by weight of the desintegrant, and from 1 to 20 by weight of the fluidizer.

7. The composition according to claim 1, which is a freeze-dried formulation manufactured by a process which comprises pulverizing the benzoyl urea compound in an aqueous solution containing the dispersant, adding the disintegrant to the resulting liquid formulation, lyophilizing the mixture, and adding the fluidizer thereto.

* * * * *